United States Patent [19]

McCutchen

[11] Patent Number: 4,677,678

[45] Date of Patent: Jun. 30, 1987

[54] ACTIVE HEARING PROTECTORS

[75] Inventor: Charles W. McCutchen, Bethesda, Md.

[73] Assignee: The United States of America as represented by the Department of Health and Human Services, Washington, D.C.

[21] Appl. No.: 630,578

[22] Filed: Jul. 10, 1984

[51] Int. Cl.[4] ............................................. A61F 11/02
[52] U.S. Cl. ............................... 381/72; 200/DIG. 2; 381/183
[58] Field of Search ........................ 381/25, 26, 72, 55, 381/57, 74, 183, 187; 179/156 A; 200/DIG. 2; 455/235, 239, 241

[56] References Cited

U.S. PATENT DOCUMENTS

| | | | |
|---|---|---|---|
| 3,549,831 | 12/1970 | Forney | 381/75 |
| 3,683,130 | 8/1972 | Kahn | 381/72 |
| 4,010,340 | 3/1977 | Palmaer | 200/DIG. 2 |
| 4,181,818 | 1/1980 | Shenier | 381/72 |
| 4,224,470 | 9/1980 | Persson et al. | 381/72 |
| 4,296,278 | 10/1981 | Cullison et al. | 381/55 |
| 4,538,296 | 8/1985 | Short et al. | 381/72 |

Primary Examiner—Forester W. Isen
Attorney, Agent, or Firm—Browdy and Neimark

[57] ABSTRACT

A hearing protective device consisting of a headset having opposite earmuff and/or earplug assemblies resiliently connected by a headband assembly including a normally open power switch closed when the headband assembly is put on the user's head. The switch controls the energizing of the electrical circuitry of the device. Each earmuff and/or earplug assembly has an outwardly-facing microphone and an inwardly-facing sound reproducer, connected to circuitry defining respective stereo channels, each channel including preamplifier circuitry and a respective power amplifier drivingly connected to one of the sound reproducers. The circuitry also includes a hyper AGC circuit which receives and sums signals from the amplifier chain and derives attenuation signals therefrom which are fed back to the amplifier circuitry and which reduces the gain of this circuitry when the input sound exceeds a certain level. This causes the inputs to the power amplifiers to fall when the input to the preamplifiers increases beyond a certain level. A balanced attenuation circuit arrangement is employed which reduces the size of too-large sound waves without altering their shape, whereby the volumes of the two stereo channels are maintained in the proper relation to each other to preserve binaural hearing.

9 Claims, 7 Drawing Figures

ACTIVE HEARING PROTECTORS

FIELD OF THE INVENTION

This invention relates to hearing protective devices, and more particularly to hearing protectors of the dual earcup or earplug type providing binaural hearing perception wherein the wearer is automatically provided with protection from high-intensity audio waves.

BACKGROUND OF THE INVENTION

It is necessary and desirable for persons working or engaging in other activities within a high noise-level environment to wear hearing protectors, such as dual earcup headsets, in order to protect their physiological hearing systems against damage from the high intensity sound. Sometimes earplugs are used rather than earcups. Sometimes, for greater attenuation, earcups are used over earplugs. Such high noise-level environments include locations near jet aircraft, target practice shooting ranges, noisy industrial plants, and the like. Various types of hearing protectors of this type have been previously proposed, such as disclosed, for example, in U.S. Pat. No. 4,064,362 to D. R. Williams, but these prior-proposed designs have relatively limited utility since they are monaural in nature. Thus, some of the proposed prior devices may provide automatic attenuation of high-volume sound waves but do not provide directional perception of different nearby sound sources. Also, some of the prior hearing protective devices may have caused distortion effects, such as changes in wave shape, making the attenuated sound unnatural and unpleasant to the hearer. At least one prior device does not cut down the electronic output when the sound is too loud but only prevents it from increasing beyond a limiting level. Another disadvantage of the prior proposed devices is proneness to being left switched on when removed from the head after a period of use, causing unnecessary battery drain, and frequently making the device unusable until the batteries have been replaced.

Thus, there is a need for a hearing protective device which provides adequate directional perception, which causes minimum wave distortion, which is automatically deenergized when taken off, and which is comfortable to wear.

SUMMARY OF THE INVENTION

Accordingly, a main object of the invention is to provide improved hearing protectors to prevent dangerously loud sounds from reaching the ears but which do not excessively attenuate sounds of safe intensity.

A further object of the invention is to provide a hearing protecting device that overcomes the deficiencies and disadvantages of the previously known hearing protective devices.

A still further object of the invention is to provide improved hearing protective devices employing automatic gain control (AGC) circuits to reduce the amplitude of excessively large audio waves without substantially altering their shapes, and wherein hyper AGC is employed, namely, wherein above a certain input level the output falls as the input rises.

A still further object of the invention is to provide improved hearing protectors of the binaural type providing directional perception along with automatic attenuation of high-intensity sound waves, thereby enabling the wearer accurately to perceive the directions of incoming sounds even if their sources are not in his field of visual perception, and also enabling the wearer to take necessary action to avoid physical damage or injury from such sources.

A still further object of the invention is to provide an improved electronic hearing protective device that automatically becomes operative when placed on the user's head, and that is automatically deenergized when taken off, thereby greatly extending the useful life of the batteries employed with the device.

A still further object of the invention is to provide an improved electronic hearing protection system of the dual earcup and/or earplug type wherein a microphone is mounted at the outside of each earcup and/or earplug, and a speaker is mounted at the inside of each earcup and/or earplug, connected in respective stereo amplifier channels with associated preamplifiers and power amplifiers, and wherein the gain of the amplifiers is controlled by a hyper AGC automatic attenuator circuit providing negative feedback to the amplifiers, consisting of AGC control voltage derived by summing the signals in the two channels, maintaining the volumes in the two channels in proper relation to each other, and preserving binaural hearing.

BRIEF DESCRIPTION OF THE DRAWINGS

Further objects and advantages of the invention will become apparent from the following description and claims, and from the accompanying drawings, wherein:

DETAILED DESCRIPTION OF A PREFERRRED EMBODIMENT

Figure 1:
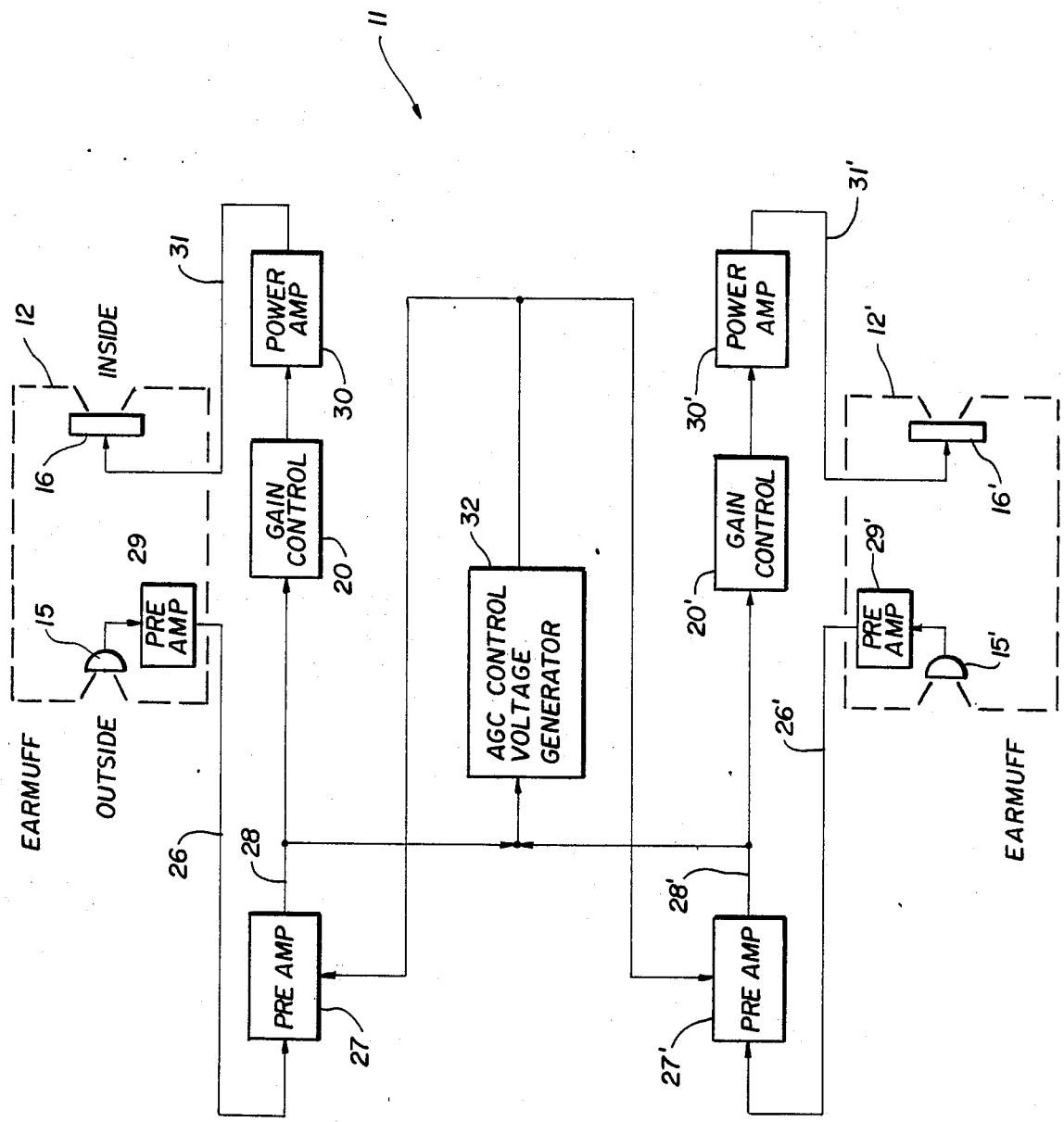
FIG. 1 is a block diagram showing a typical dual audio-transducer binaural hearing protection system according to the present invention.
Figure 3:
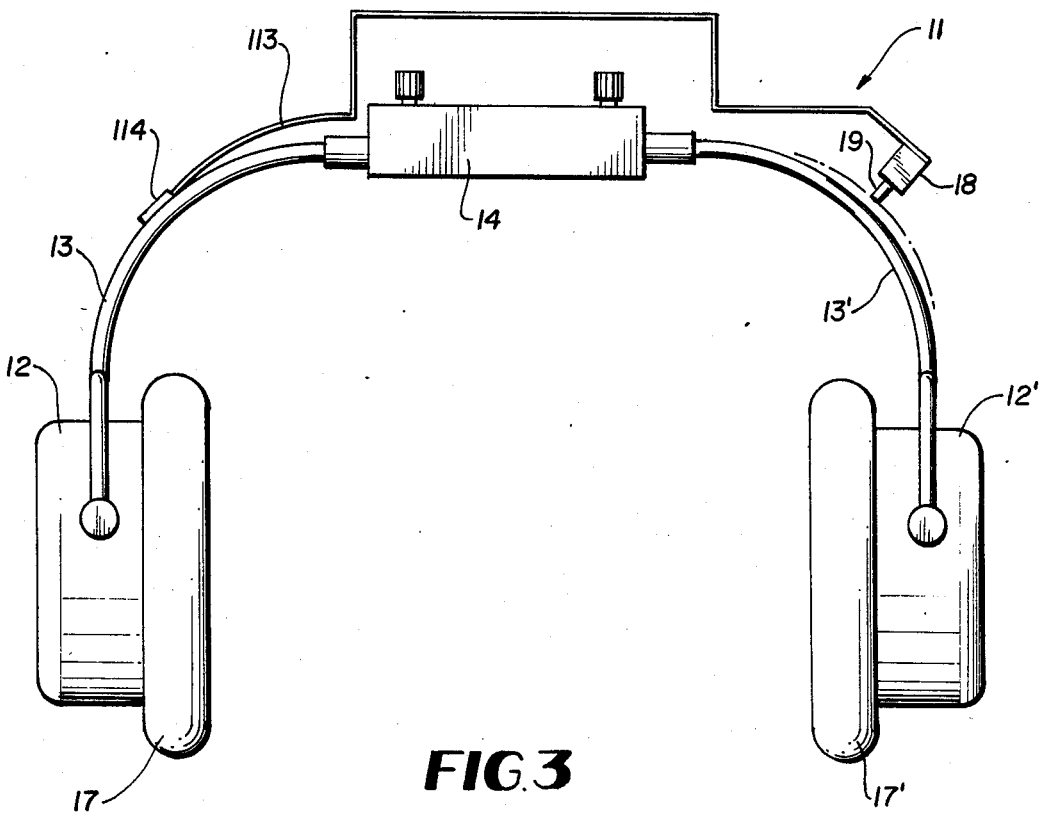
FIG. 3 is an elevational view of an improved dual audio-transducer hearing protective device employing the circuitry of FIGS. 1 and 2.

Referring to the drawings, and more particularly to FIGS. 1 and 3, 11 generally designates an improved binaural hearing protector device according to the present invention. The device 11 comprises a dual audio-transducer arrangement which has opposite earcup or "earmuff" assemblies 12 and 12', connected together by a resilient headband assembly comprising resilient arcuate spring members 13 and 13'. In the specific embodiment illustrated in FIG. 3, the inner ends of the members 13 and 13' are rigidly connected to opposite ends of an elongated housing 14 which contains the electrical circuitry of the device, except for microphones, speakers, a switch presently to be described, and the associated external wiring.

A support arm 113 is rigidly connected at 114 to the midportion of member 13 and extends over housing 14 to overlie member 13' approximately at its midportion. A microswitch 18 is secured to the free end of arm 113 with its operating plunger 19 directed toward flexible member 13' and being operatively engageable thereby when the headset is put on the user's head.

Although the embodiment illustrated in the drawings employs speakers 16, 16' as the dual audio-transducers, it will be understood that conventional earplugs may be employed as the audio-transducers instead of speakers, and that the earplugs may be mounted inside earmuffs for increased attenuation.

Thus, the earmuff assembly 12 contains an outwardly-facing microphone 15 mounted on its outer side portion and an inwardly-facing small speaker 16, mounted to transmit sound inwardly substantially at the center of an ear-sealing pad member 17 in which the users's right ear is receivable. Similarly, the opposite earmuff assembly 12' contains an outwardly-facing microphone 15' mounted on its outer side portion and an inwardly-facing small speaker 16' mounted to transmit sound inwardly substantially at the center of an ear-sealing pad member 17' in which the user's left ear is receivable.

The respective earmuff assemblies 12 and 12' are pivotally connected to the resilient spring members 13, 13' in a conventional manner to allow the pad members 17, 17' to sealingly engage around the wearer's ears. As above mentioned, the normally open power supply microswitch 18 is mounted on the free end of arm 113. Spreading the spring members 13, 13' to put the headset unit on one's head causes member 13' to push on the plunger 19 of the microswitch and turn it on.

Figure 4:
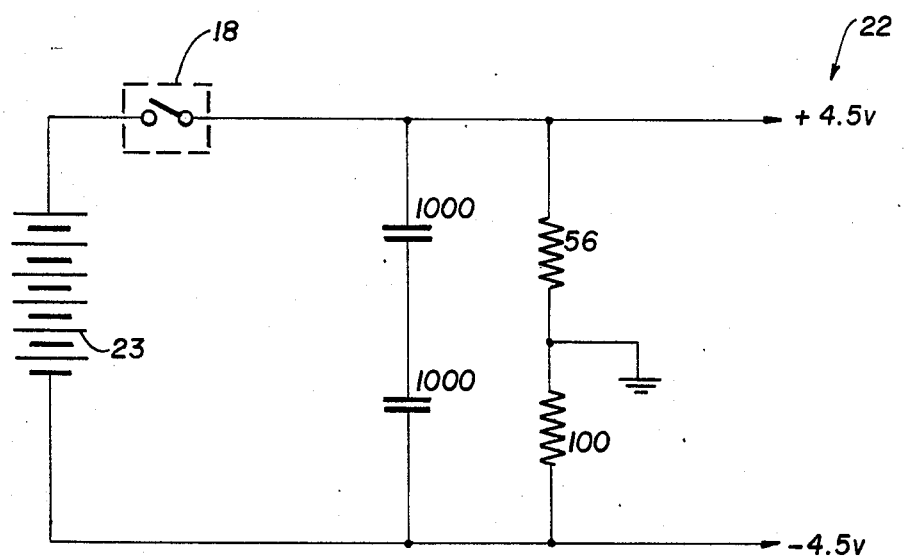
FIG. 4 is a wiring diagram of the power supply circuit employed in the dual audio-transducer hearing protective device of FIGS. 1 to 3.

The power supply, designated at 22, is substantially conventional in design, and includes a replaceable or rechargeable 9-volt battery 23. The circuitry of the power supply is arranged to provide respective output voltages of +4.5 volts and −4.5 volts, with a common center ground, as shown in FIG. 4. The power supply 22, including the battery 23, is contained in the housing 14.

Figure 2:
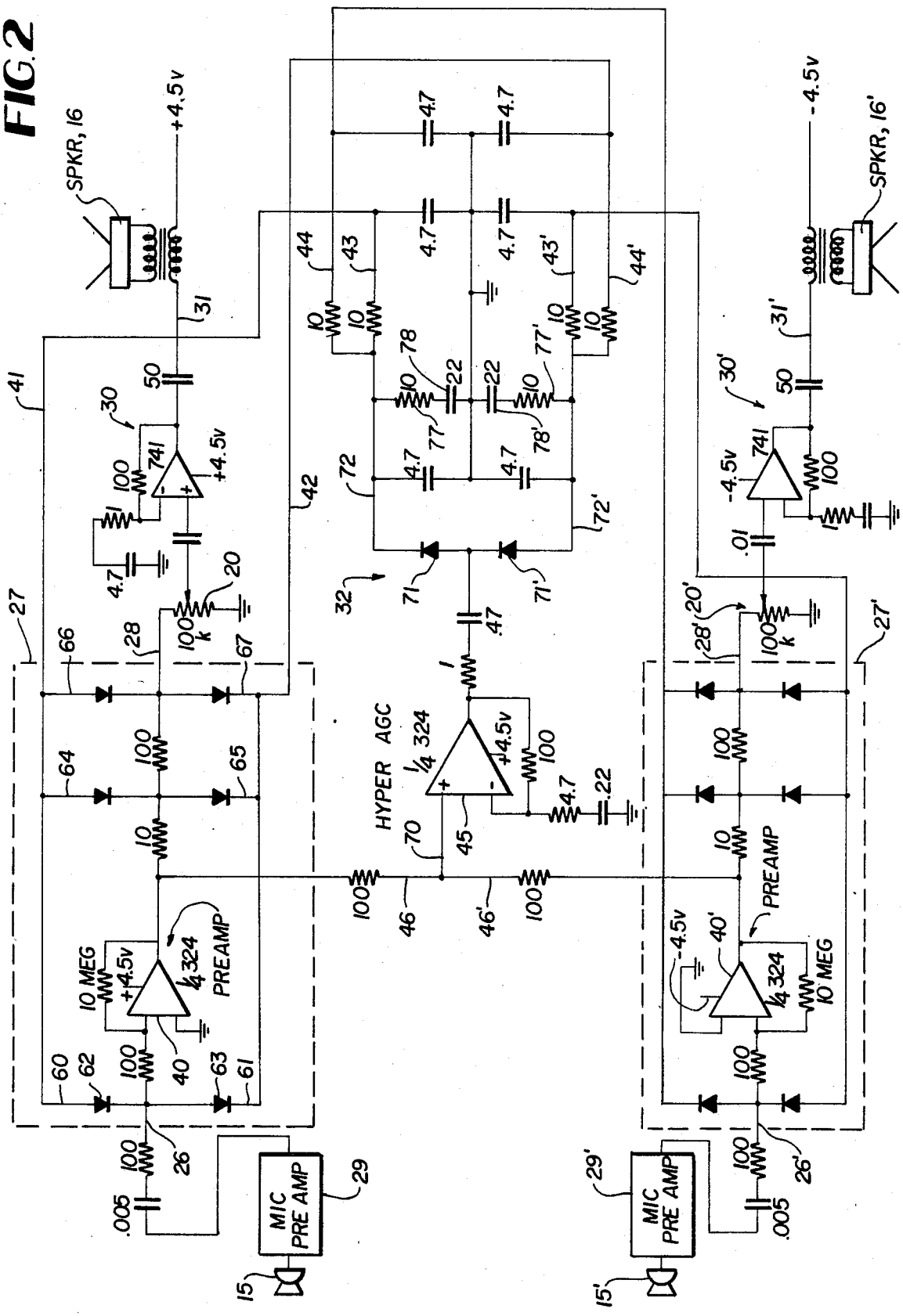
FIG. 2 is a wiring diagram of a system according to FIG. 1.

Referring to FIGS. 1 and 2, it will be seen that the output of microphone 15 is fed via a built-in first preamplifier 29 to a feed line 26, said feed line 26 being connected to the input of a second preamplifier circuit 27. The output line 28 of said second preamplifier circuit is connected to the input of a conventional power amplifier circuit 30 via a manual gain control potentiometer 20. The output line 31 of power amplifier circuit 30 is connected to the speaker 16.

Similarly, the output of microphone 15' is fed via a built-in first preamplifier 29' to a feed line 26' leading to the input of a second preamplifier circuit 27'. The output line 28' of the second preamplifier circuit 27' is connected via gain control potentiometer 20' to the input of a second conventional power amplifier circuit 30' whose output line 31' is connected to the speaker 16'.

Hyper AGC circuitry 32 is employed to automatically control the gain of the preamplifier circuits 27, 27'. Thus, amplifier circuit 27 includes an amplifier 40 which receives input from preamplifier 29, attenuated by gain control signals received from the hyper AGC circuitry 32 via gain control lines 41, 42 from output lines 43, 44 of network 32. Said network 32 includes a summing amplifier 45 fed by summing lines 46, 46' with output signals from the amplifiers 40, 40' of amplifier circuits 27, 27'. Ideally, powers rather than amplitudes should be summed, or the summing should be done after rectification. Both solutions introduce more components. In summing amplitudes there is a theoretical danger that signals from the two channels will be equal in amplitude and opposite in phase, thus cancelling each other and providing less attenuation than is needed. In reality, practical waveforms are complicated in shape and the effect is not noticeable. The output network of the amplifier 40 also receives attenuation signals from lines 41, 42 in accordance with the summed signals of lines 46, 46'. A similar attenuating action occurs with respect to the input and output signals of the amplifier 40' of the amplifier circuit 27'. The use of proper component values, such as those shown in FIG. 2, provides hyper AGC, namely above a certain input level the output to the volume controls 20, 20' falls as the input to the amplifier circuits 27, 27' rises. Even though the amount of direct sound transmission through the earmuffs 12, 12' may also be rising, still the total sound presented to the user's ears is roughly independent of the input level in this range. Therefore, the total sound heard by the ears at high input levels is reduced to a safe value.

Balancing of the gain in the two sterio channels is provided by potentiometers forming gain controls 20, 20'. With components shown, this permits gains to range from zero to slightly more than unity, for the benefit of deaf users.

The balanced circuit arrangement shown in FIG. 2 reduces the size of too-large sound waves without altering their shape, and maintains the volumes of the two stereo channels in the proper relation to each other, thus preserving binaural hearing.

As shown in FIG. 2, the output currents from amplifiers 40, 40' travel via lines 46, 46' and are summed in the input line 70 of AGC amplifier 45. The outputs to respective lines 44, 43 and 44', 43' are rectified via diodes 71, 71' in output branches 72, 72' leading to the lines 44, 43 and 43', 44'. Line 44 feeds line 42 and line 43 feeds line 41. The circuitry associated with output branch 72' is symmetrically similar to that of output branch 72.

As shown in FIG. 2, the diode chains 60-61, 62-63 and 64-65 lie between the signal path and the lines 41 and 42 which have low impedance. Their dynamic resistance decreases with the forward current through them. In conjunction with the resistors in the signal path feeding them they form variable attenuators whose attenuations increase with bias current provided by lines 41 and 42. These currents increase with the amplitude of the input signals and will tend to keep the output of the intermediate amplifier from exceeding a limiting value. Because two of the attenuators come after this point in the signal path, the final output signal falls with input amplitude once the latter is high enough.

The desired threshold levels and transient response control for generating and sustaining the necessary attenuation feedback currents are established by suitably selecting the values of the associated resistance and capacitance components employed in the hyper AGC network 32, particularly the R-C discharge branches 77, 78 and 77', 78' associated with the lines 72 and 72'.

Since the attenuation signal is a function of the sum of the sound intensities applied to both channels, it acts to attenuate the signals evenly in said channels and therefore does not affect their relative amplitudes. Therefore there is minimum wave distortion, and directional perception is not adversely affected by the attenuation of signal strength in the two channels.

The microphone preamplifiers 29, 29' may be built into the earmuff assemblies 12, 12' or may be located in the same housing 14 as the remaining electrical circuitry if so desired.

Figure 5:
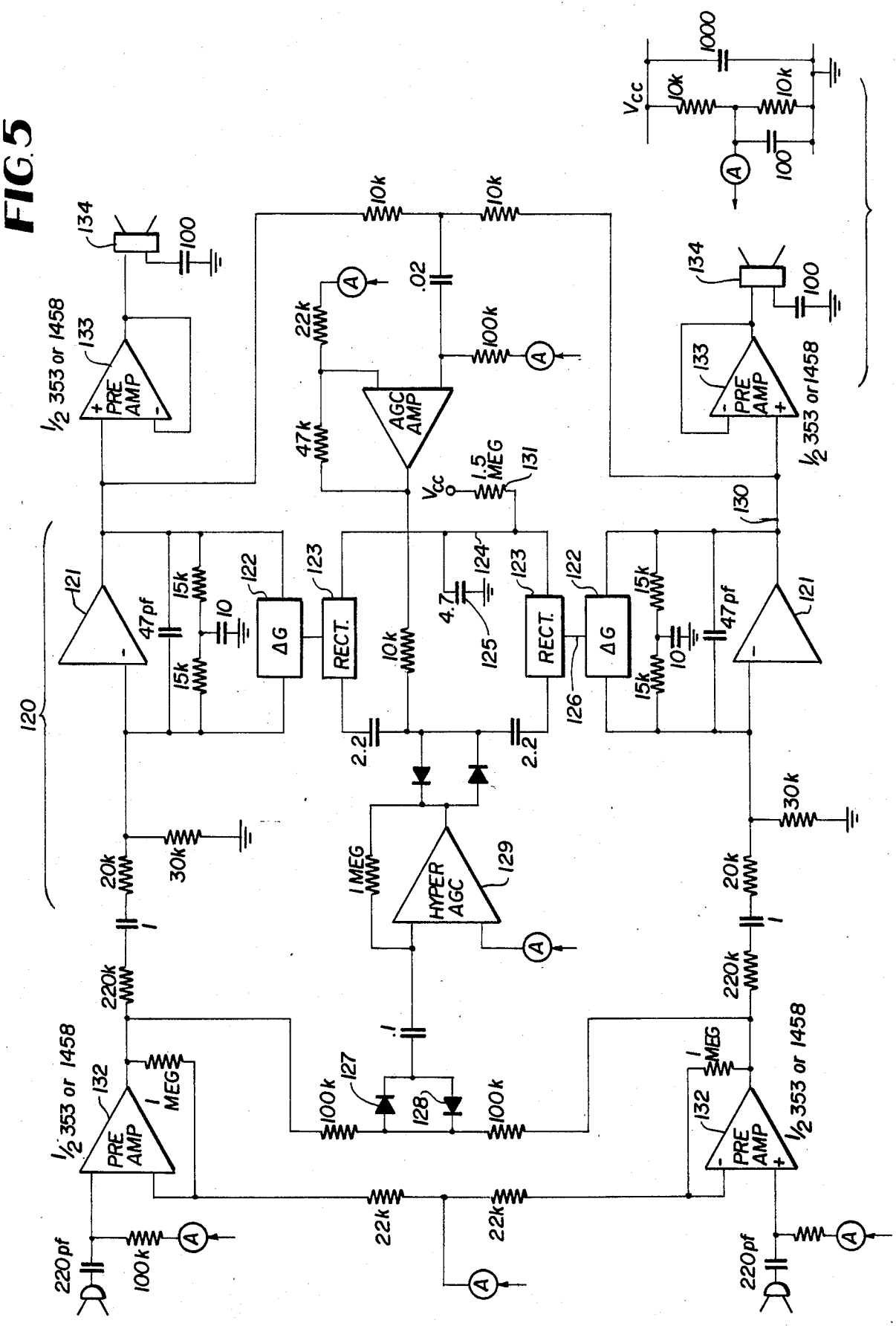
FIG. 5 is a wiring diagram of a modified dual audio-transducer hearing protective device according to the present invention.

An alternative circuit, shown in FIG. 5, uses a "compandor" circuit shown generally at 120, as the gain controlling element. The circuit 120 has two separate signal channels, each comprising an operational amplifier 121, a variable gain amplifier 122 and a rectifier 123. A signal applied to the rectifier 123 charges a control terminal 124 whose potential determines the gain of the variable gain amplifier 122. An external capacitor 125 attached to the control terminal 124 sets the attack and release times of the device. The attack and release times are in fixed proportion to each other set by internal components of the circuit 120.

The circuit of FIG. 5 uses the circuit 120 as a compressor. To do this, the variable gain amplifier 122 (of each channel) is put in the feedback path of the operational amplifier 121, whose output is also applied via wire 126 to the rectifier 123. The feedback signal is thus proportional to the square of the output. Since the feedback signal must be equal in magnitude to the input signal (and opposite in sign, since the operational amplifier inverts) the output at 126 is proportional to the square root of the input.

This gain characteristic attenuates high level signals without entirely abolishing differences in loudness. To the listener it is unobtrusive. It must, however, be modified at both top and bottom ends. As the signal level rises, the sound level at the ear eventually approaches 90 dB. Hyper AGC is then provided by arranging that as this level is approached, the signal picked off a point in the input chain exceeds a threshold set by two parallel oppositely polarized diodes 127, 128. The portion of the signal in excess of the diode drop is amplified by the hyper AGC amplifier 129 and is applied to the rectifier 123 input. The result is that the output at 130 falls with further increase in input. In the typical illustrated circuit it falls to one third its largest amplitude.

With the square root law, the gain rises indefinitely as the signal level falls. By injecting current at the gain control terminal 124 via the 1.5 megohm resistor 131, the output/input relation is made to change smoothly from square law to linear as the input falls to conversational levels. Increasing the value of resistor 131 raises the gain in the linear region for deaf users.

Additional components are used to overcome limitations of the circuit 120. The preamplifiers 132 are present not because the unit 120 lacks adequate gain, but because it is noisy. The AGC amplifier 129 reduces the gain of the unit 120 in the square root region. If the rectifiers 123 are supplied directly by the output, the unit gives too large an output unless its input is so small that it approaches the noise level. The output unity-gain power amplifiers 133 are used because the circuit unit otherwise suffers cross-over distortion if it drives the 100-ohm speakers 134 directly.

Figure 6:
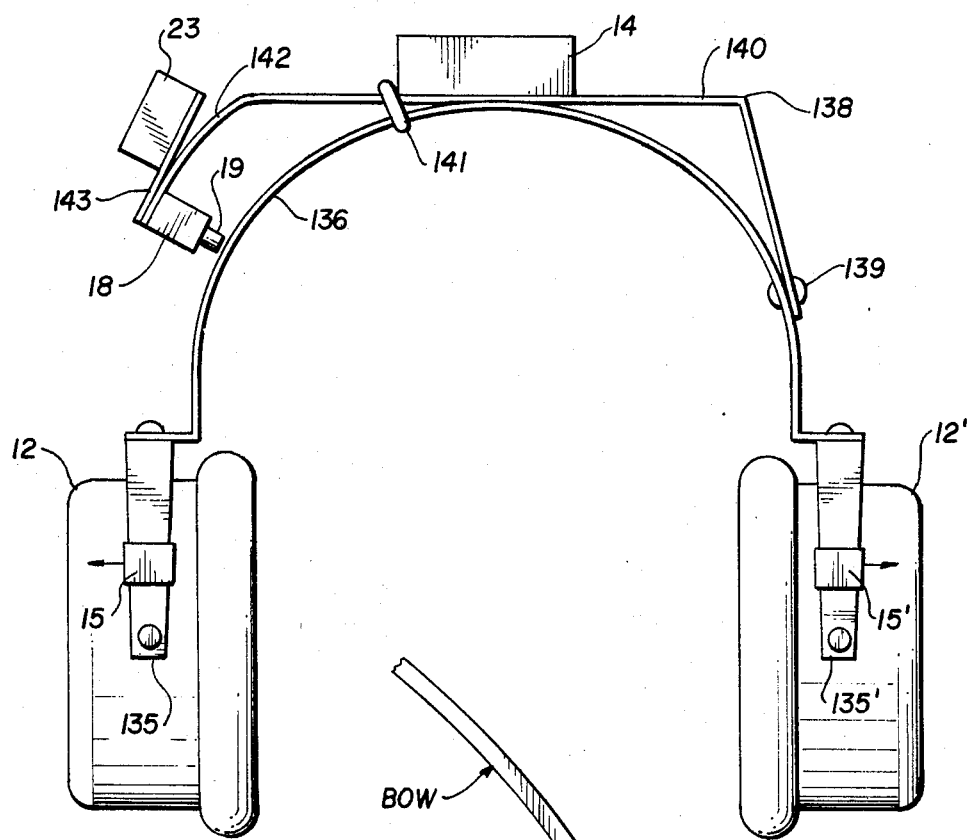
FIG. 6 is an elevational view of another form of dual audio-transducer hearing protective device employing circuitry of the present invention and including an automatic energizing switch.

In the embodiment shown in FIG. 6, the ear muff assemblies 12, 12' are pivotally mounted in respective clevis members 135, 135' supportingly connected to the opposite ends of a resilient bow or headband member 136. The outwardly-facing microphones 15, 15' are fixedly mounted on the front depending arms of the clevis members 135, 135'. A supporting top arm 138 extends over the bow member 136 and is bolted at 139 to one side of the bow member 136. The electronic package 14 is mounted on the horizontal intermediate portion 140 of support arm 138. A rubber band 141 surrounds the arm element 140 and bow member 136 leftwardly adjacent to the electronic package 14, as viewed in FIG. 6, resiliently binding arm portion 140 to bow member 136. Arm portion 140 has a downwardly inclined left end portion 142, to the end of which is secured the normally open microswitch 18, with its operating plunger 19 extending toward and being operatively engageable by the leftward portion of bow member 136. A supporting plate 143 is secured on the lower end of portion 142 and carries the battery assembly 23. Outward flexure of the left side portion of the bow member 136 when the headband is placed on the user's head closes microswitch 18 and energizes the apparatus.

Figure 7:
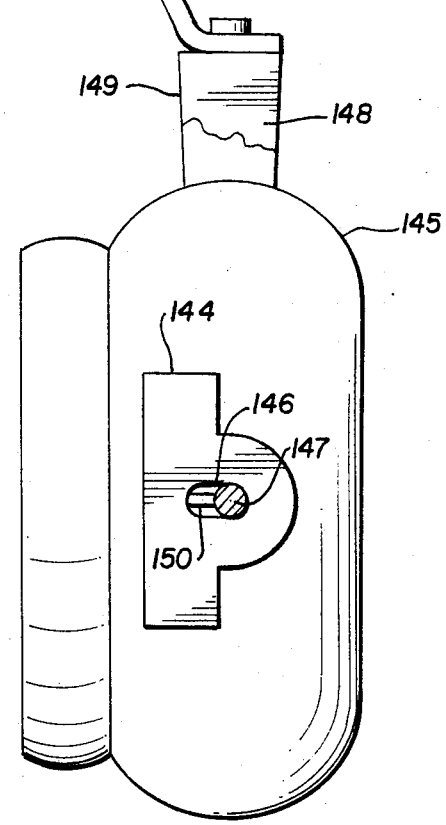
FIG. 7 is an enlarged front elevational view, partly in cross section, showing another form of automatic energizing switch device which may be employed with an earmuff in a hearing protective system according to the present invention.

In the embodiment shown in FIG. 7, the power control microswitch, shown at 144, is fixedly mounted directly on one of the earmuffs, shown at 145. The microswitch housing is slotted horizontally at 146 to slidably receive the transversely-extending front clevis pin 147 carried by the front arm 148 of the earmuff clevis member 149. The normally open microswitch 144 has an operating plunger 150 operatively engageable with clevis pin 147 to close the microswitch responsive to the rightward movement of the earmuff 145, as viewed in FIG. 7, when the headband is put on the user's head, whereby to energize the apparatus.

While certain specific embodiments of improved hearing protective devices have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A hearing protective device comprising
a headset having a headband;
audio transducer assemblies secured to opposite ends of said headband;
each of said audio transducer assemblies including a microphone and a sound reproducer;
circuit means including two respective stereo audio channels connecting said microphone and said sound reproducer of each of said respective audio transducer assemblies;
attenuation circuit means having an input connected to receive simultaneously the outputs of said microphones;
said attenuation circuit means including
means to generate two symmetrically similar attenuation current signals with amplitudes in accordance with the combined outputs of said microphones;
said generating means including
hyper automatic gain control circuitry means to substantially progressively lower output currents of said stereo audio channels as the combined outputs of said microphones continue to rise after exceeding a predetermined level;
and means to feed back the respective attenuation current signals to said stereo audio channels at locations therein which affect respective output currents of said stereo audio channels;
said headset having movable switching means mounted thereon to switch said headset on and off.

2. The hearing protective device of claim 1 wherein said switching means is operated by movement of at least one of said audio transducer assemblies relative to the other of said assemblies.

3. The hearing protective device of claim 2 wherein said switching means is connected to said stereo audio channels and said attenuation circuit means; said switching means including
a normally open power switch mounted on said headset,
and means closing said power switch responsive to the placement of said headset on the user's head.

4. The hearing protective device of claim 3 wherein said normally open power switch is supportingly mounted on said headband;
said power switch is provided with a movable operating member located on said headset in a position to be operatively engaged by a side portion of said headband.

5. The hearing protective device of claim 1 wherein each said stereo audio channel includes an amplifier; and said attenuation circuit means includes
circuit means to apply attenuation current signals simultaneously both at the input and output of said amplifier.

6. The hearing protective device of claim 1 wherein each said stereo audio channel includes
a first amplifier driven by an associated one of said microphones,
and a second amplifier driven by said first amplifier;
and said attenuation circuit means includes
circuit means to apply attenuation current signals simultaneously to the input and output of said second amplifier.

7. The hearing protective device of claim 6 wherein each said stereo audio channel includes
a power output amplifier,
and circuit means connecting the output of said second amplifier to the input of said power output amplifier.

8. The hearing protective device of claim 1 wherein each said stereo audio channel includes
a plurality of distinct impedance means,
and said means to feed back the respective attenuation current signals to said stereo audio channels in said attenuation circuit means includes
circuit means to apply attenuation current signals simultaneously to a plurality of spaced portions located at opposite sides of said impedance means.

9. The hearing protective device of claim 1 wherein each said stereo audio channel includes
a plurality of successive amplifiers,
and said means to feed back the respective attenuation current signals to said stereo audio channels in said attenuation circuit means includes
circuit means to simultaneously apply the attenuation current signals to the input and the output of at least one of said plurality of successive amplifiers.

* * * * *